United States Patent
Sivagurunathan et al.

(10) Patent No.: US 12,110,530 B2
(45) Date of Patent: Oct. 8, 2024

(54) PROCESS FOR SECOND GENERATION LACTIC ACID PRODUCTION

(71) Applicants: Indian Oil Corporation Limited, Mumbai (IN); Department Of Biotechnology, New Delhi (IN)

(72) Inventors: Periyasamy Sivagurunathan, Faridabad (IN); Alok Satlewal, Faridabad (IN); Tirath Raj, Faridabad (IN); Ravindra Kumar, Faridabad (IN); Ravi Prakash Gupta, Faridabad (IN); Suresh Kumar Puri, Faridabad (IN); Sankara Sri Venkata Ramakumar, Faridabad (IN)

(73) Assignees: Indian Oil Corporation Limited, Mumbai (IN); Department Of Biotechnology, New Delhi (IN)

( * ) Notice: Subject to any disclaimer, the term of this patent is extended or adjusted under 35 U.S.C. 154(b) by 48 days.

(21) Appl. No.: 17/691,912

(22) Filed: Mar. 10, 2022

(65) Prior Publication Data
US 2022/0290195 A1  Sep. 15, 2022

(30) Foreign Application Priority Data
Mar. 10, 2021 (IN) .............................. 202121010021

(51) Int. Cl.
| | | |
|---|---|---|
| C12P 7/56 | (2006.01) | |
| C12P 7/10 | (2006.01) | |
| C12P 19/14 | (2006.01) | |

(52) U.S. Cl.
CPC .................. *C12P 7/56* (2013.01); *C12P 7/10* (2013.01); *C12P 19/14* (2013.01); *C12P 2201/00* (2013.01); *C12P 2203/00* (2013.01)

(58) Field of Classification Search
CPC .... C12P 7/56; C12P 7/10; C12P 19/14; C12P 2201/00; C12P 2203/00; C12R 2001/225
See application file for complete search history.

(56) References Cited

U.S. PATENT DOCUMENTS

| 10,240,171 B2 | 3/2019 | Baets et al. |
| 2011/0177567 A1 | 7/2011 | Bakker et al. |
| 2015/0125917 A1 | 5/2015 | Walsh et al. |
| 2015/0197777 A1 | 7/2015 | Adhikari et al. |

FOREIGN PATENT DOCUMENTS

| EP | 3587584 A1 | 1/2020 |
| WO | 2009025547 A1 | 2/2009 |
| WO | 2011049205 A1 | 4/2011 |
| WO | 2013050584 A1 | 4/2013 |

OTHER PUBLICATIONS

Anuradha et al., Simultaneous saccharification and fermentation of starch to lactic acid. Process Biochem., 1999, vol. 35: 367-375. (Year: 1999).*
Novozymes, Application Sheet, Cellic® CTec2 and HTec2-Enzymes for hydrolysis of lignocellulosic materials. 2010, 9 pages downloaded Jun. 15, 2023. (Year: 2010).*
Shivankari et al., Bioproduction of Lactic Acid Exposed to Metronidazole. Biotech Today, 2020, vol. 10(1): 43-45. (Year: 2020).*
Wang et al., Pretreatment of corn stover by solid acid for D-lactic acid fermentation. Biores. Technol., 2017, vol. 239: 490-495. (Year: 2017).*
Abe et al., Comparison of the characteristics of cellulose microfibril aggregates of wood, rice straw and potato tuber Cellulose, 2009, vol. 16: 1017-1023. (Year: 2009).*
Zhang et al., Biorefinery approach for cassava-based industrial wastes: Current status and opportunities Biores. Technol., 2016, vol. 215: 50-62. (Year: 2016).*
Zhu et al., Structural features affecting biomass enzymatic digestibility. Biores. Technol., 2008, vol. 99: 3817-3828. (Year: 2008).*
Bondesson, Pia-Maria, Galbe, Mats, "Process design of SSCF for ethanol production from steam-pretreated, acetic-acid-impregnated wheat straw", Biotechnology for Biofuels, 9:222, Oct. 18, 2016.
Grewal, J., Khare, S.K., "One-pot bioprocess for lactic acid production from lignocellulosic agro-wastes by using ionic liquid stable Lactobacillus brevis", Bioresource Technology, Dec. 18, 2017, doi: https://doi.org/10.1016/j.biortech.2017.12.056.
Jiang et al., "Lactic Acid Production from Pretreated Hydrolysates of Corn Stover by a Newly Developed Bacillus coagulans Strain", PLoS One 11(2), Feb. 10, 2016, DOI:10.1371/journal.pone.0149101.
Li et al., "Quantitative chemocatalytic production of lactic acid from glucose under anaerobic conditions at room temperature", The Royal Society of Chemistry, Green Chem., Oct. 20, 2016, 19, 76-81.
Ouyang et al., "Open fermentative production of L-lactic acid by *Bacillus* sp. strain NL01 using lignocellulosic hydrolyzates as low-cost raw material", Bioresource Techology, 135, Oct. 5, 2012, 475-480.
Raj et al., "Physical and Chemical Characterization of Various Indian Agriculture Residues for Biofuels Production", Energy & Fuels, Apr. 27, 2015, 29, 3111-3118.

(Continued)

*Primary Examiner* — Ganapathirama Raghu
(74) *Attorney, Agent, or Firm* — Workman Nydegger

(57) ABSTRACT

The present invention provides an improved process for high titer lactic acid production using simultaneous saccharification and co-fermentation process using acid treated lignocellulosic biomass. The process comprises of pretreating lignocellulosic biomass comprising C5 and C6 sugars with dilute acid and superheated steam at a temperature ranging from 150-210° C.; neutralizing the pretreated lignocellulosic biomass of step (i) with NaOH pellets; and adding cellulase enzyme in the range of 1.5 to 10 FPU/g, bacteria, nutrients and buffering agent to the neutralized slurry obtained in step (ii) for hydrolysis and co-fermentation of C5 and C6 sugars at a temperature ranging from 40-45° C. for a period of 120-144 hours to obtain lactic acid. The process of the present invention requires simple nutrients and results in high titer lactic acid production within shortest duration of time.

10 Claims, 1 Drawing Sheet

(56) References Cited

OTHER PUBLICATIONS

Itu et al., "Physical and Chemical Characterization of Various Indian Agriculture Residues for Biofuels Production", BioResources, Mar. 27, 2019, 14(2), 3873-3885, DOI: 10.15376/biores.14.2.3873-3885.
Wischral et al., "Lactic Acid Production from Sugarcane Bagasse Hydrolysates by Lactobacillus pentosus: Integrating Xylose and Glucose Fermentation", Biotechnology Progress, 35(1), Oct. 2018, DOI: 10/1002/btpr.2718.
Yi et al., "Engineering wild-type robust Pediococcus acidilactici strain for hightiter l- and d-lactic acid production from corn stover feedstock", Journal of Biotechnology, 217, Nov. 20, 2015, 112-121.
Zhang et al., "An efficient process for lactic acid production from wheat straw by a newly isolated Bacillus coagulans strain IPE22", Bioresource Technology, 158, Mar. 12, 2014, 396-399.
Zhang et al., "D-Lactic Acid Production from Renewable Lignocellulosic Biomass via Genetically Modified Lactobacillus plantarum", Biotechnology Progress, Jan. 8, 2016, 32(2), 271-278.
Zhao et al., "Optimization of microwave pretreatment of lignocellulosic waste for enhancing methane production: Hyacinth as an example", Front. Environ. Sci. Eng., Jul. 16, 2017, 11(6): 17.

\* cited by examiner

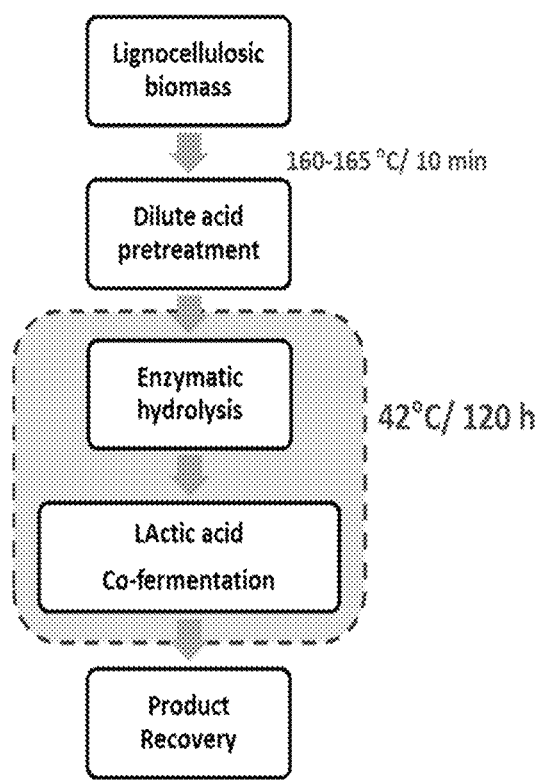

PROCESS FOR SECOND GENERATION LACTIC ACID PRODUCTION

FIELD OF THE INVENTION

The present invention relates to a process for production of lactic acid from lignocellulosic biomass. More particularly, the present invention provides an improved process for high titer lactic acid production using simultaneous saccharification and co-fermentation process using acid treated biomass.

BACKGROUND OF THE INVENTION

With economic growth and enhanced energy demand worldwide, the fossil fuel consumption has also increased, therefore various chemical industries are actively exploring the possibilities for the development of the biobased economy for production of fuels and chemicals by replacing the fossil-based economy. Ethanol fuel is being produced from Lignocellulosic Biomass (LCB) across the world. However, the cost of ethanol produced from LCB is higher than the fuel 1G ethanol. Therefore, a biorefinery based concept is being developed to improve the economics of the 2G bioethanol process and to reduce the dependency on fossil-based fuels for chemical commodities production.

Lignocellulosic biomass is most abundant, renewable available organic material on the globe for production of industrial chemicals, i.e., lactic acid, acetic acid, propionic acid and ethanol fuel. LCB mainly consists of 50-60% of polymerized sugars (Zhao et al., 2017). Although these polymeric sugars in lignocellulosic biomass are entrapped in complex recalcitrance matrix of cellulose (a polymer of $\beta$-1,4-glucan), hemicelluloses (i.e., xylans, glucans, mannans, arabinans etc.), lignin phenylpropanoid polymer), extractives, ash etc. (Raj et al., 2015), thus, the breakdown of intrinsic recalcitrance cell wall matrix is highly essential to release the polymeric sugars for enzymatic saccharification. Further, the entrapped polymeric sugars in LCBs must be hydrolyzed into fermentable sugars to be used by lactic acid bacteria. In 2G bio refinery, pretreatment is initially performed over LCBs, which helps to disintegrate the crystalline complex structure of biomass and make it accessible for cellulase for enzymatic saccharification to make biomass digestible by enzymes. Thus, the effective combination of a thermo-chemical pretreatment and enzymatic hydrolysis is necessary for monomeric sugars production which on fermentation can be converted into lactic acid to avoid the cumbersome process of solid-liquid separation and washing of pretreated slurry, which causes major obstacle in industrial scale production.

Lactic acid (LA) is the most promising acid and widely used in food, pharmaceutical, cosmetic, chemical industries etc. LA serves as an intermediate precursor for production of various commodity chemicals and polymers, i.e., bioplastic, preservatives, additives and acrylic acids etc. For instance, PLA (polylactic acid) is one of the polymers used for the preparation of biocompatible thermoplastic, which could be synthesized from lactic acid.

Conventionally, LA is synthesized from high-grade sugar resources, i.e., molasses, glucose or starch microbial fermentation. Presently, commercially, $3.3 \times 10^5$ tons of LA is produced annually by the biochemical process. (Li et al., 2016). However, due to limited availability of $1^{st}$ generation sugar-rich crops and food vs. fuels competition, exploration of alternative feedstock is a hot area of research now a days. Therefore, development of an efficient and cost-effective approach for lactic acid fermentation from cheaper and non-food sugar substrates is favored these days. Current 2G biorefinery processes are facing lot of financial crises due to the high cost of production. Hence, the coupling of lactic acid fermentation with 2G ethanol process may improve the economics of the process. Therefore, to address the above commercialization challenges for bio-based production, very limited research work was performed with in situ saccharification and co-fermentation into lactic acid using lactic acid production bacteria. In recent study, (Grewal & Khare et al., 2018) showed a holistic approach for SSCF of ionic liquid treated cottonseed cake, wheat straw and sugarcane bagasse in one pot process, which yielded 0.22, 0.49 and 0.52 g/g of lactic acid using *Lactobacillus brevis* strain. Similarly, (Zhang et al., 2016) performed the SSCF of corn stiver and sorghum stalks using *L. plantarum* strains, which yielded 27.3, 22.0 g/L of lactic acid with a productivity of 0.75 and 0.65 g/L/g respectively.

SHCF and SSCF processes for biocatalytic conversion of lignocellulosic biomass to lactic acid have been disclosed in the prior arts. Each process has a unique advantage, the separate hydrolysis and co-fermentation process involves the operation of enzymatic hydrolysis (50-52° C.) and fermentation (30-42° C.) separately at their optimal conditions. However, the feed-back inhibition and high enzyme loading requirement limit their process scale up, during high solid loading input for biomass hydrolysis and fermentation. On the other hand, the simultaneous saccharification and co-fermentation (SSCF) process operates at a temperature range suitable for enzyme hydrolysis and fermentation, preferably at 37-42° C., wherein the releases sugars and simultaneous bioconversion of the released sugars to lactic acid and reduces the risk of feedback inhibition of sugar and other by-products formed during the fermentation process.

US 2015/0125917 A1 describes a method for separate hydrolysis and co-fermentation process for the bioconversion of lignocellulosic biomass to lactic acid. The document describes the usage of steam-explosion pretreated biomass for enzymatic hydrolysis and fermentation of lactic acid in a separate process using a *Lactobacillus coryniformis* subsp. *Torquens*. However, the process resulted in the conversion efficiency of 65% of lignocellulosic sugars to lactic acid with a lactic acid production titer of ~40 g/L.

WO 2013/050584 A1 relates to a method for production of carboxylic acids like lactic acid from monomeric sugars derived from lignocellulosic biomasses using novel *Thermoanaerobacter* sp. strain. The document describes the use of sulphuric acid catalyzed steam pretreatment for lignocellulosic biomass and enzymatic hydrolysis of pretreated slurry using saccharolytic enzymes. The process showed about 20 g/L of lactic acid with a total of ~70 g/L of total product formed.

WO 2011/049205 A1 describes SHCF method for production of lactic acid from plant biomass without any sterilization procedure. The document particularly, describes the use of alkaline solution such as caustic soda for lignin separation from biomass at 50-120° C. Sugar rich solution was obtained using cellulase (Novozymes). Further, also describes a method for producing lactic acid, which comprises culturing an alkaliphilic lactic acid bacterium *Enterococcus casseriflavus* L-120 in a culture medium containing a cellulose saccharified solution under non-sterile conditions at pH 9-11 and further culturing the resulting culture at pH 5-9.

US20110177567A1 relates to a method for production of organic acids as a fermentation product from lignocellulosic biomass, wherein the lignocellulosic biomass is pretreated using an alkaline agent at pH 8 to 14.0 The patent document describes the simultaneously saccharification and fermentation (SSF) of the alkaline-pretreated wheat straw by *B. coagulans*, in a fed-batch manner, yielding ~40.1 g/L of lactic acid after 55 hours of incubation, which accounted for 43% (w/w) of the theoretical yield.

U.S. Pat. No. 10,240,171 B2 relates to a method for lactic acid production from lignocellulosic biomass by separate saccharification and fermentation steps. The document describes the use of alkali pretreated biomass for enzyme hydrolysis and fermentation of lactic acid using non-GMO strain *Bacillus coagulans* DSM 2314. The process produced a lactic acid concentration of 58 g/L.

WO 2009/025547 A1 relates to a method for SSCF for the bioconversion of lignocellulosic biomass to lactic acid. It discloses the usage of alkaline pretreated biomass for simultaneous saccharification and fermentation of lactic acid using non-GMO strain *Bacillus coagulans* DSM 2314. The process comprises an initial prehydrolysis step for 2 hours, followed by enzymatic hydrolysis and fermentation. The process resulted in a lactic acid production titer of 40.7 g/L with 0.74 g/L/h. The hydrolysis efficiency of the glucan and xylan conversion present in the pretreated biomass was noted as 55 and 75%, respectively.

US 2015/0197777 A1 discloses a consolidated bioprocessing one-step process for lactic acid production from lignocellulosic biomass. The invention uses *Paenibacillus macerans* IIPSP3 (MTCC 5569) for lignocellulosic biomass hydrolysis and lactic acid production under aerobic conditions. However, the process used complex nutrients for microbial growth, low solid loading and poor conversion efficiency of sugars to lactic acid production.

EP 3 587 584 A1 discloses a pretreatment method for lignocellulosic biomass with less amount of inhibitors (HMF, furfural, acetic acid, and formic acid) formation and subsequent enzymatic hydrolysis step for improved sugar conversion with low enzyme dosage.

Microbial conversion of lignocellulosic biomass to lactic acid has been reported by various non-patented documents. For example, Jiang, T et al., PloS one, 11(2), used an acid pretreated and undetoxified condensed acid-catalyzed steam-exploded hydrolysate (CASEH) for lactic acid production by *B. coagulans* NL01 and the process produced 45 g/L of lactic acid with a productivity of 0.46 g/L/h. In another report, Yi et al. Journal of biotechnology, 217, 112-121 used engineered *Pediococcus acidilactici* bacteria for lactic acid production from dilute acid pretreated and biodetoxified corn stover with high solid loading content of 25% (w/w) an SSF process. The process produced a 76 g/L of lactic acid and demonstrated that removal of inhibitor played a significant role in the enhancement of lactic acid production. The accumulations of lactic acid by the engineered strains were strongly dependent on inhibitors removal extent by biodetoxification. Another report, Ouyang et al. 2013 Bioresource technology, 135, 475-480 demonstrated lactic acid production from corn stover by *B. coagulans* NL01 and reported 56 g/L of lactic acid was obtained from lignocellulosic hydrolyzates which contained the solid residues produced in enzymatic saccharification. In fed-batch fermentation, 75.03 g/L L-lactic acid was obtained from lignocellulosic hydrolyzates supernatant. The yield was 74.5% and the average productivity was 1.04 g/L/h.

Tu et al. 2019 describes production of lactic acid from lignocellulosic biomass in an integrated simultaneous saccharification and fermentation process using isolated bacterium strain *Lactobacillus plantarum*. The bacterium strain eliminated the need for detoxification processes that removes fermentation inhibitors. The process resulted in final lactic acid concentration of 65.6 g/L with a cellulose-to-lactic acid yield of 69%.

Zhang et al., 2014 relates to a process wherein lactic acid is produced from wheat straw. Particularly, a thermophilic lactic acid (LA) producer is isolated and identified as *Bacillus coagulans* strain IPE22. The strain showed capability to ferment pentose, hexose and cellobiose, and is also resistant to inhibitors from lignocellulosic hydrolysates.

Galbe et al., 2016 describes a study to improve ethanol production from glucose and xylose in steam-pretreated, acetic-acid-impregnated wheat straw by process design of simultaneous saccharification and co-fermentation (SSCF), using a genetically modified pentose fermenting yeast strain *Saccharomyces cerevisiae*.

Wischral et al. 2018 describes a study regarding the use of sugarcane bagasse hydrolysates for lactic acid production by *Lactobacillus* spp. Particularly, five strains of *Lactobacillus* spp. are investigated for one that had the ability to consume xylose efficiently. Subsequently, biomass fractionation is performed by dilute acid and alkaline pretreatments, and the hemicellulose hydrolysate (HH) fermentability by the selected strain is carried out in bioreactor.

Although, available literature provides several methods for lactic acid production, however, the available methods face several challenges. Thus, there is a need in the art to develop a method of lactic acid production which results in higher productivity with lesser nutrient requirements.

SUMMARY OF THE INVENTION

In an aspect of the present invention, there is provided an improved process for production of lactic acid from a lignocellulosic biomass, the process comprising:
  i. pretreating lignocellulosic biomass comprising C5 and C6 sugars with dilute acid and superheated steam at a temperature ranging from 150-210° C.
  ii. neutralizing the pretreated lignocellulosic biomass of step (i) with NaOH pellets;
  iii. adding cellulase enzyme in the range of 1.5 to 10 FPU/g, bacteria, nutrients and buffering agent to the neutralized slurry obtained in step (ii) for hydrolysis and cofermentation of C5 and C6 sugars at a temperature ranging from 40-45° C. for a period of 120-144 hours to obtain lactic acid.

In an embodiment of the present invention, there is provided a process wherein the pretreatment of biomass slurry additionally comprises adjusting pH of the slurry to 5.0-5.5 with a pH adjuster.

In another embodiment of the present invention, there is provided a process wherein the pH adjuster is selected from aqueous ammonium hydroxide, NaOH, KOH and $CaCO_3$.

In yet another embodiment of the present invention, there is provided a process wherein the nutrient is yeast extract and diammonium hydrogen phosphate $(NH_4)_2HPO_4$.

In still another embodiment of the present invention, there is provided a process wherein the buffering agent is calcium carbonate ($CaCO_3$).

In an embodiment of the present invention, there is provided a process wherein the pre-treated biomass slurry is subjected to fermentation without any detoxification.

In another embodiment of the present invention, there is provided a process wherein the bacteria is *Lactobacillus* selected from *Lactobacillus lactis* 2369 (NCIM) and *Lactobacillus delbrueckii* 2365 (NCIM). The *Lactobacillus lactis* 2369 (NCIM) and *Lactobacillus delbrueckii* 2365 (NCIM) bacteria is publicly available and purchased from National Collection of Industrial Microorganisms (NCIM) National Chemical Laboratory Dr. Homi Bhabha Road, Pune 411008, India on Jul. 10, 2018, and Dec. 6, 2018.

In yet another embodiment of the present invention, there is provided a process wherein the lignocellulosic biomass is selected from the group consisting of rice straw, wheat straw, sugarcane bagasse, cotton stalk, barley stalk, bamboo or any agriculture residues which contain cellulose or hemicellulose or both.

In still another embodiment of the present invention, there is provided a process wherein the C5 sugar is xylose and C6 sugar is glucose.

In an embodiment of the present invention, there is provided a process wherein the process yields ~90 g/L lactic acid within 120 hours of fermentation.

In another embodiment of the present invention, there is provided a process wherein the fermentation reaction is a batch process.

In an aspect of the present invention, there is provided a process for production of lactic acid from lignocellulosic biomass using a pretreated slurry, wherein simultaneous saccharification and co-fermentation is performed.

These and other features, aspects, and advantages of the present subject matter will be better understood with reference to the following description. This summary is provided to introduce a selection of concepts in a simplified form.

BRIEF DESCRIPTION OF DRAWINGS

These and other features, aspects, and advantages of the present invention will become better understood when the following detailed description is read with reference to the accompanying drawings in which like characters represent like parts throughout the drawings wherein:

FIG. 1 illustrates the overall steps involved in SSCF process for lactic acid production from lignocellulosic biomass.

DETAILED DESCRIPTION OF THE INVENTION

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

Definition

For the purposes of this invention, the following terms will have the meaning as specified therein:

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to" "including" and "including but not limited to" are used interchangeably.

Nearly all forms of lignocellulosic biomass, i.e., plant biomass, such as monocots, comprise three primary chemical fractions: hemicellulose, cellulose, and lignin. Cellulose and hemicelluloses in plant cell walls exist in complex structures within the residual material. Hemicellulose is a polymer of short, highly-branched chains of mostly five-carbon pentose sugars (xylose and arabinose), and to a lesser extent six-carbon hexose sugars (galactose, glucose and mannose). Because of its branched structure, hemicellulose is amorphous and relatively easy to hydrolyze into its individual constituent sugars by enzyme or dilute acid treatment. Cellulose is a linear polymer comprising of β (1→4) linked D-glucose in plant cell wall, much like starch with a linear/branched polymer comprising of a (1→4) linked D-glucose, which is the primary substrate of corn grain in dry grain and wet mill ethanol plants. However, unlike starch, the glucose sugars of cellulose are strung together by β-glycosidic linkages which allow cellulose to form closely-associated linear chains. Because of the high degree of hydrogen bonding that can occur between cellulose chains, cellulose forms a rigid crystalline structure that is highly stable and much more resistant to hydrolysis by chemical or enzymatic attack than starch or hemicellulose polymers.

Therefore, a pretreatment process is typically used to alter and open up the cell wall matrix, to hydrolyze the hemicelluloses, and to reduce crystallinity. Pretreatment disrupts the non-easily digestible portion of lignocellulosic biomass, e.g., cellulose and lignin, thus improving its digestibility. After pretreatment, much of the biomass becomes easily digestible while a portion remains non-easily digestible. Ultimately, the pretreatment process makes the cellulose and/or hemicellulose more accessible (during a subsequent hydrolysis process) for conversion of the carbohydrate polymer into fermentable sugars.

Cellulase enzyme" used herein is a mixed form of enzyme which is mostly composed of exo-hydrolase, endo-hydrolase and beta-glucosidase and other auxiliary enzymes. Cellulase breaks down the cellulose molecule into monosaccharide and shorter polysaccharides or oligosaccharides and the cellulase enzyme were obtained from Novozymes.

"Pretreated biomass" or "Pretreatment of biomass" used herein clears away physical and chemical barriers that make native biomass recalcitrant and exposes cellulose for better enzymatic hydrolysis. In most of the pretreatment, chemical (acid or alkali) and physical (high temperature or steam or pressure) parameters are used individually or in mixed manner to remove barriers for enzymatic hydrolysis and improve the enzymatic digestibility.

"Detoxification" used herein is the process where the inhibitors (toxic compound such hydroxymethyl furfural, furfural, acetic acids, formic acids etc.) produced during the pretreatment process are removed or neutralized from pretreated biomass by chemical, physical or biological process.

The present invention relates to bioconversion of acid-treated biomass for high-titer lactic acid production with lesser nutrient requirements, operation with high solid loading and low enzyme loading resulting in a cost-effective lactic acid production.

The objective of the present invention is to produce high titer lactic acid from waste lignocellulosic biomass in one pot simultaneous saccharification and co-fermentation process (SSCF). Particularly, the present invention provides a process for production of lactic acid from lignocellulosic biomass using a dilute acid pretreatment, wherein the pretreatment method solubilizes maximum of hemicelluloses and improves the digestibility of cellulose rich pretreated slurry using commercial cellulases. The dilute acid pretreated lignocellulosic biomass comprises soluble C5 and solid C6 sugars for enzymatic hydrolysis. This is followed by co-fermentation of C5 and C6 sugars present in the pretreated biomass with a cellulase enzyme, bacteria and nutrient to obtain lactic acid in a single unit system with a fixed temperature regime for effective lactic acid production.

Thus, according to one aspect of the present invention, there is provided an improved process for production of lactic acid from a lignocellulosic biomass, the process comprising:
  i. pretreating lignocellulosic biomass comprising C5 and C6 sugars with dilute acid and superheated steam at a temperature ranging from 150-210° C.
  ii. neutralizing the pretreated lignocellulosic biomass of step (i) with NaOH pellets; and
  iii. adding cellulase enzyme in the range of 1.5 to 10 FPU/g, bacteria, nutrients and buffering agent to the neutralized slurry obtained in step (ii) for hydrolysis and cofermentation of C5 and C6 sugars at a temperature ranging from 40-45° C. for a period of 120-144 hours to obtain lactic acid.

In an embodiment of the present invention, there is provided a process for the production of lactic acid, wherein the pretreatment of biomass slurry additionally comprises adjusting pH of the slurry to 5-5.5 with a pH adjuster.

In another embodiment of the present invention, there is provided a process for production of lactic acid, wherein the pH adjuster used for adjusting pH of the slurry is selected from aqueous ammonium hydroxide, NaOH, KOH and $CaCO_3$.

In yet another embodiment of the present invention, there is provided a process for production of lactic acid, wherein the nutrient is yeast extract and diammonium hydrogen phosphate $(NH_4)_2HPO_4$.

In still another embodiment of the present invention, there is provided a process for production of lactic acid, wherein the buffering agent is calcium carbonate ($CaCO_3$).

In an embodiment of the present invention, there is provided a process for production of lactic acid, wherein the pre-treated biomass slurry is subjected to fermentation without any detoxification.

The production of lactic acid is commonly carried out by fermentation of a strain of the bacterial genus *Lactobacillus* and more particularly by the species *Lactobacillus delbrueckii, Lactobacillus acidophilus, Lactobacillus acidophilus, Lactobacillus rhamnosus, Lactobacillus pentosus* and *Lactobacillus lactis* as examples. In a preferred embodiment of the present invention, the *Lactobacillus* is selected from *Lactobacillus lactis* 2369 (NCIM) and *Lactobacillus delbrueckii* 2365 (NCIM). The *lactobacillus* species used in the present invention is capable of utilizing both glucose and xylose fraction of the pretreated biomass and results in high-titer lactic acid production.

In an embodiment of the present invention, there is provided a process for production of lactic acid, wherein the lignocellulosic biomass is selected from the group consisting of rice straw, wheat straw, sugarcane bagasse, cotton stalk, barley stalk, bamboo or any agriculture residues which contain cellulose or hemicellulose or both.

In another embodiment of the present invention, there is provided a process for production of lactic acid, wherein C5 sugar is xylose and C6 sugar is glucose.

In an embodiment of the present invention, there is provided a process for production of lactic acid, wherein the process yields ~90 g/L lactic acid within 120 hours of fermentation.

In another embodiment of the present invention, the biomass loading of 10 to 25% (w/w) was used for lactic acid production. In a preferred embodiment of the present invention, high solid loading of 25% (w/w) is used for high-titer lactic acid production.

In an embodiment of the present invention, there is provided a process for production of lactic acid, wherein the fermentation reaction is a batch process.

In an aspect of the present invention, there is provided a process for production of lactic acid from lignocellulosic biomass using a pretreated slurry wherein simultaneous saccharification and co-fermentation is performed.

Thus, the process of the present invention produces high titer lactic acid from waste lignocellulosic biomass in one pot simultaneous saccharification and co-fermentation process (SSCF). The process claimed in the present invention requires simpler nutrients for microbial growth and fermentation can be performed in an open with no sterilization. Further, high solid loading of 25% (w/w) and low enzyme dosage (1.5 to 10 FPU/g biomass) is required for lactic acid fermentation. In addition, the results obtained in the fermentation process as indicated in Table 2-4 of examples demonstrates that the strains *Lactobacillus lactis* and *Lactobacillus delbrueckii* used in the process results in high-titer lactic acid production from pretreated biomass via SSCF process.

Although the subject matter has been described in considerable detail with reference to certain preferred embodiments thereof, other embodiments are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods, the exemplary methods, devices and materials are described herein. It is to be understood that this disclosure is not limited to particular methods, and experimental conditions described, as such methods and conditions may vary.

Example 1: Preparation of Pretreated Lignocellulosic Biomass

For the preparation of lignocellulosic biomass, rice straw (*Oryza sativa*), agricultural waste material was collected from a field near Mathura, Uttar Pradesh (27.28° N 77.41° E) during harvesting period. The rice straw was air dried and shredded to 10 mm size using a knife cutting mill and was further, preserved using sealed poly bags maintained at room temperature (25° C.) for experimentation. Table 1 indicates chemical composition of native biomass and pretreated biomass. The dilute acid pretreatment of shredded rice straw was conducted using in-house designed (250 kg/day) continuous pilot-scale reactor system using dilute sulfuric acid (1.8%). The plant consists of a size reduction mill, high-pressure reactor, screw feeder, hydraulic press, slurry tank and feed hoper. Milled rice straw (10 mm) was presoaked in an acid solution (1.8%) for a duration of 30 minutes. Further, acid-soaked biomass was then pressed to reduce the excess water ~50% and soaked biomass was fed through feed hopper at a flow rate of 10 Kgh$^{-1}$. Rice straw was pretreated at the optimized temperature at ~162° C. and 5.2 bar for a residence time of 10 minutes using superheated steam. After dilute acid pretreatment, the pretreated slurry was collected and cooled down to room temperature and the chemical composition were determined by the NREL method (NREL/TP-510-42621).

TABLE 1

Chemical Compositional analysis of native and pretreated rice straw

| Biomass | Extractive | Glucan | Xylan | Lignin | Ash |
|---|---|---|---|---|---|
| Native biomass | 18 | 38.94 | 17.57 | 17.73 | 9.33 |
| Pretreated biomass | 0 | 42.51 | 17.22 | 28.53 | 14.95 |

Water extractives; Ethanol extractives; Glucan and Xylan were calculated using NREL Lap equations

Example 2: Simultaneous Hydrolysis and Co-Fermentation Process (SSCF) for Lactic Acid Production by *Lactobacillus lactis* 2369

For the lactic acid production, first dilute acid pretreated rice straw was neutralized with NaOH pellets to pH 4.8-5.0. The pretreated neutralized slurry was added with commercial cellulase enzyme using 5 FPU/g of cellulase per gram of substrate, yeast extract (1%), $(NH_4)_2PO_4$ (0.1%) and $CaCO_3$ (~0.45 g/g total sugar), 10% (v/v) of *Lactobacillus lactis* 2369 NCIM culture and fermentation was performed in a single step. The simultaneous hydrolysis and co-fermentation process was performed in batch mode by maintaining the reactor temperature at 42° C. for a duration of 120-144 hours with a fixed rpm of 200. Table 2 below indicates the lactic acid production and acetic acid production by using dilute acid pretreated rice straw. It was observed that the final lactic acid production was 108 g/L. All aqueous samples were analyzed by HPLC to determine lactic acid and by-product concentrations using Waters HPLC equipment (Water, Switzerland) equipped with HPX 87H and HPX 87 P column (Bio-Rad Labs, USA) and Waters Refractive index (RI 2414) and Waters UV-vis spectrophotometer (2489) measuring at a wavelength 210 nm. A racemic mixture of lactic acid (D/L), with D-lactic acid as a major fraction was obtained, as evident from D/L-lactic colorimetric assay kit.

TABLE 2

SSCF process of lactic acid production using *Lactobacillus lactis*

| Substrate | #Initial Glucose concentration (g/L) | #Initial xylose concentration (g/L) | Fermentation time (h) | Final Lactic acid Titer(g/L) | Final Acetic acid Titer (g/L) |
|---|---|---|---|---|---|
| Dilute acid pretreated rice straw | 10.3 | 33.6 | 120 | 108.1 | 11.5 |

Initial sugar concentration is measured in the feed slurry before adding the seed culture

Example 3: Simultaneous Hydrolysis and Co-Fermentation Process (SSCF) for Lactic Acid Production by *Lactobacillus delbrueckii* 2365

The bacterial strain *Lactobacillus delbrueckii* is evaluated to demonstrate lactic acid production from C5 and C6 sugars of the pretreated lignocellulosic biomass. In this process, at first dilute acid pretreated rice straw was neutralized with NaOH pellets to pH 4.8-5.0 as described in Example 2. Neutralized (20~25 wt. % on dry weight), commercial cellulase (5 FPU/g), yeast extract (1%), $(NH_4)_2PO_4$ (0.1%) and $CaCO_3$ (~0.45 g/g total sugar) and 10% (v/v) of *Lactobacillus delbrueckii* NCIM culture was added in single go. Simultaneous hydrolysis and co-fermentation process were performed in batch mode by maintaining the reactor temperature at 42° C. Table 3 below indicates the lactic acid production and acetic acid production by using strain *Lactobacillus delbrueckii* 2365. It was observed that lactic acid concentration of 97 g/L is achieved within 120 hours of reaction. The strain produces a homogenous mixture of L-Lactic acid (L), as evident from D/L-lactic colorimetric assay kit.

TABLE 3

SSCF process of lactic acid production using *Lactobacillus delbrueckii*

| Substrate | #Initial Glucose concentration (g/L) | #Initial xylose concentration (g/L) | Fermentation time (h) | Final Lactic acid Titer(g/L) | Final Acetic acid Titer (g/L) |
|---|---|---|---|---|---|
| Dilute acid pretreated rice straw | 10.3 | 33.6 | 120 | 97.4 | 9.7 |

Initial sugars concentration is measured in the feed slurry before adding the seed culture Example 4 Simultaneous Hydrolysis and Co-Fermentation Process (SSCF) for Lactic Acid Production Via Co-Culture of *Lactobacillus delbrueckii* 2365 and *Lactobacillus lactis* 2369

In this process, a co-culture of *Lactobacillus delbrueckii* and *Lactobacillus lactis* is demonstrated for lactic acid production from C5 and C6 sugars of the pretreated lignocellulosic biomass with a mixing ration of 1:1. In this process, at first dilute acid pretreated rice straw was neutralized with NaOH pellets to pH 4.8-5.0. Neutralized (20~25 wt. % on dry weight), commercial cellulase (5 FPU/g), yeast extract (1%), $(NH_4)_2PO_4$ (0.1%) and $CaCO_3$ (~0.45 g/g total sugar), 5% (v/v) of *Lactobacillus delbrueckii* and 5% (v/v) of *Lactobacillus lactis* were added in single go. Simultaneous hydrolysis and co-fermentation process were performed in batch mode by maintaining the reactor temperature at 42° C. The result obtained (depicted in Table 4 below) indicates that by using the co-culture of *Lactobacillus lactis* and *Lactobacillus delbrueckii*, the lactic acid concentration of 82 g/L was observed in 120 hours of reaction. The strains produces a racemic mixture of Lactic acid (D/L), as evident from D/L-lactic colorimetric assay kit.

TABLE 4

SSCF process of lactic acid production using co-culture of *Lactobacillus lactis* and *Lactobacillus delbrueckii*

| Substrate | #Initial Glucose concentration (g/L) | #Initial xylose concentration (g/L) | Fermentation time (h) | Final Lactic acid Titer(g/L) | Final Acetic acid Titer (g/L) |
|---|---|---|---|---|---|
| Dilute acid pretreated rice straw | 10.3 | 33.6 | 120 | 82.8 | 9.7 |

Initial sugars concentration is measured in the feed slurry before adding the seed culture

We claim:

1. A process for production of a lactic acid from a lignocellulosic biomass, the process consisting of:
  i. pretreating the lignocellulosic biomass with a dilute acid and a superheated steam at a temperature in a range of 150-210° C., wherein the lignocellulosic biomass consists of C5 and C6 sugars C to obtain a pretreated lignocellulosic biomass;
  ii. neutralizing the pretreated lignocellulosic biomass of step (i) with NaOH pellets to obtain a neutralized biomass slurry; and
  iii. adding a cellulase enzyme in a range of 1.5 to 5 filter-paper units/gram, a *Lactobacillus* bacteria, nutrients, and a buffering agent to the neutralized biomass slurry obtained in step (ii) for hydrolysing and co-fermenting the C5 and the C6 sugars at a temperature in a range of 40-45° C. for a period of 120-144 hours to obtain the lactic acid,
  wherein the *Lactobacillus* bacteria is selected from the group consisting of *Lactobacillus lactis* 2369 (NCIM) and *Lactobacillus delbrueckii* 2365 (NCIM),
  wherein the lignocellulosic biomass is selected from the group consisting of rice straw, wheat straw, sugarcane bagasse, cotton stalk, barley stalk, bamboo, and agriculture residues, wherein the agricultural residues comprise cellulose, hemicellulose, or both, and wherein hydrolysing and co-fermenting are carried out in a single unit system.

2. The process as claimed in claim 1, wherein the pretreatment of neutralized biomass slurry further comprises adjusting pH of the neutralized biomass slurry to 5.0-5.5 with a pH adjuster.

3. The process as claimed in claim 2, wherein the pH adjuster is selected from the group consisting of an aqueous ammonium hydroxide, NaOH, KOH and CaCO3.

4. The process as claimed in claim 1, wherein the nutrients is selected from the group consisting of yeast extract and diammonium hydrogen phosphate (NH4)2HPO4.

5. The process as claimed in claim 1, wherein the buffering agent is calcium carbonate (CaCO3).

6. The process as claimed in claim 1, wherein the pretreated neutralized biomass slurry is subjected to fermentation without detoxification.

7. The process as claimed in claim 1, wherein the C5 sugar is xylose and the C6 sugar is glucose.

8. The process as claimed in claim 1, wherein the process yields ~90 g/L lactic acid within 120 hours of fermentation.

9. The process as claimed in claim 1, wherein the fermentation reaction is a batch process.

10. The process as claimed in claim 1, wherein producing lactic acid comprises producing lactic acid by simultaneous saccharification and co-fermentation of the lignocellulosic biomass.

* * * * *